United States Patent [19]
Ceravolo

[11] Patent Number: 5,957,964
[45] Date of Patent: *Sep. 28, 1999

[54] MULTICHAMBERED ICE CAP

[76] Inventor: Frank J. Ceravolo, 1971 E. Commercial Blvd., Ft. Lauderdale, Fla. 33308

[*] Notice: This patent issued on a continued prosecution application filed under 37 CFR 1.53(d), and is subject to the twenty year patent term provisions of 35 U.S.C. 154(a)(2).

[21] Appl. No.: 08/603,904

[22] Filed: Feb. 29, 1996

[51] Int. Cl.$^6$ ........................................... A61F 7/00
[52] U.S. Cl. .................... 607/109; 607/110; 607/112; 607/114
[58] Field of Search ................. 607/104, 108–112, 607/114

[56] References Cited

U.S. PATENT DOCUMENTS

| | | | |
|---|---|---|---|
| 683,991 | 10/1901 | Rowe | 607/110 |
| 2,049,723 | 8/1936 | Pomeranz | 150/2.3 |
| 3,159,160 | 12/1964 | Ullom | 128/97 |
| 3,349,825 | 10/1967 | Andreadis | 607/110 |
| 3,491,761 | 1/1970 | Baker | 128/402 |
| 3,696,814 | 10/1972 | Umemoto | 128/380 |
| 4,138,743 | 2/1979 | Elkins | 2/171.2 |
| 4,356,709 | 11/1982 | Alexander | 62/530 |
| 4,551,858 | 11/1985 | Pasternack | 2/7 |
| 4,781,193 | 11/1988 | Pagden | 128/402 |
| 5,163,425 | 11/1992 | Nambu et al. | 128/380 |
| 5,261,399 | 11/1993 | Klatz et al. | 607/109 X |

*Primary Examiner*—Jeffrey R. Jastrzab
*Assistant Examiner*—Ryan Carter
*Attorney, Agent, or Firm*—Oltman, Flynn & Kubler

[57] ABSTRACT

Flexible icecaps for overlying the top of a user's head. The icecaps have plural chambers formed between inner and outer flexible material layers. A first embodiment includes an ice cap having a front chamber two side chambers and a rear chamber which are each separated from one another wherein at least one chamber can be filled with a coolant liquid such as ice, so that icecap can be partially used for localized headaches. A second embodiment includes two front chambers, on the right and left side, and two rear chambers, on the right and rear side. Chin straps can be used to hold the cap in place. Elastic bands can be used to separate each of the chambers and aid in elastically holding the cap in place on the user's head. Waterproof portals can be used to access each of the chambers on the top of the icecap. Portals can be either screw on caps or rubberized plugs. A third embodiment includes a single flexible layer shaped as a helmet to fit over the head of a user. The outer surface of the layer can have hook and loop type fasteners wherein individual prefilled pouches of coolant liquid having hook and loop fasteners on an exterior surface can be mounted to the exterior of the flexible layer. Alternatively, the exterior surface can have pockets with side openings sized to snugly receive prefilled pouches of coolant liquid.

13 Claims, 4 Drawing Sheets

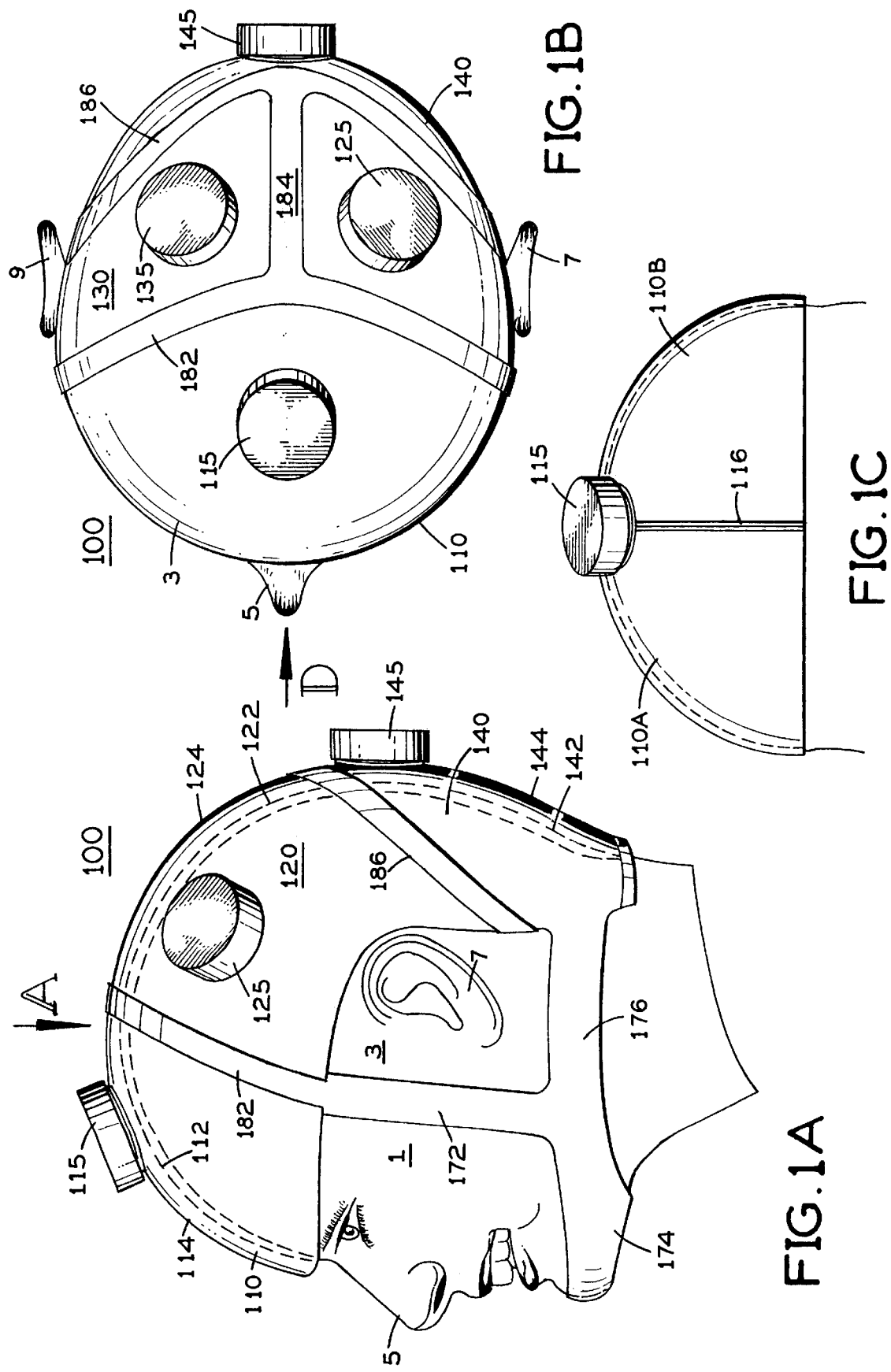

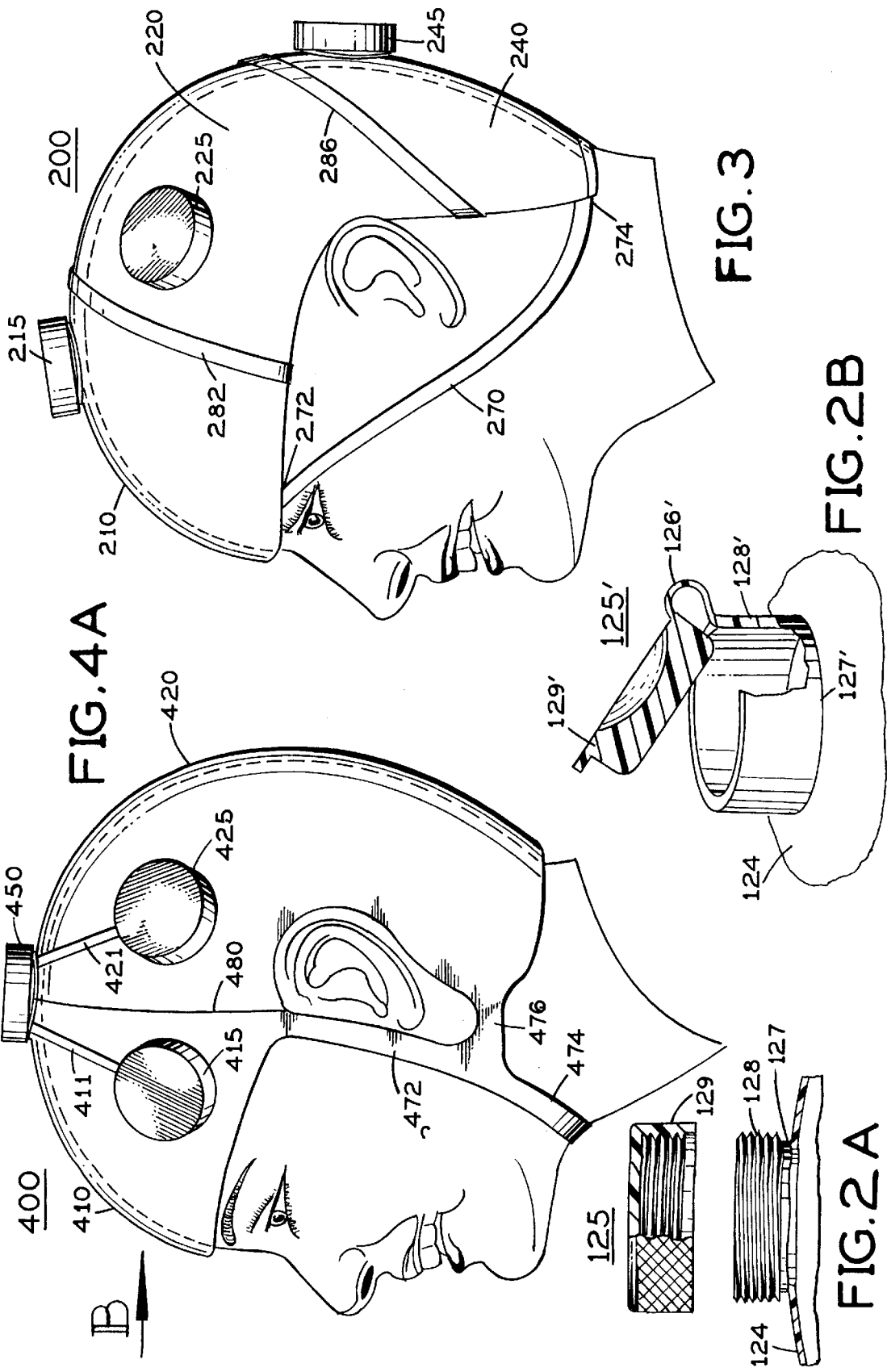

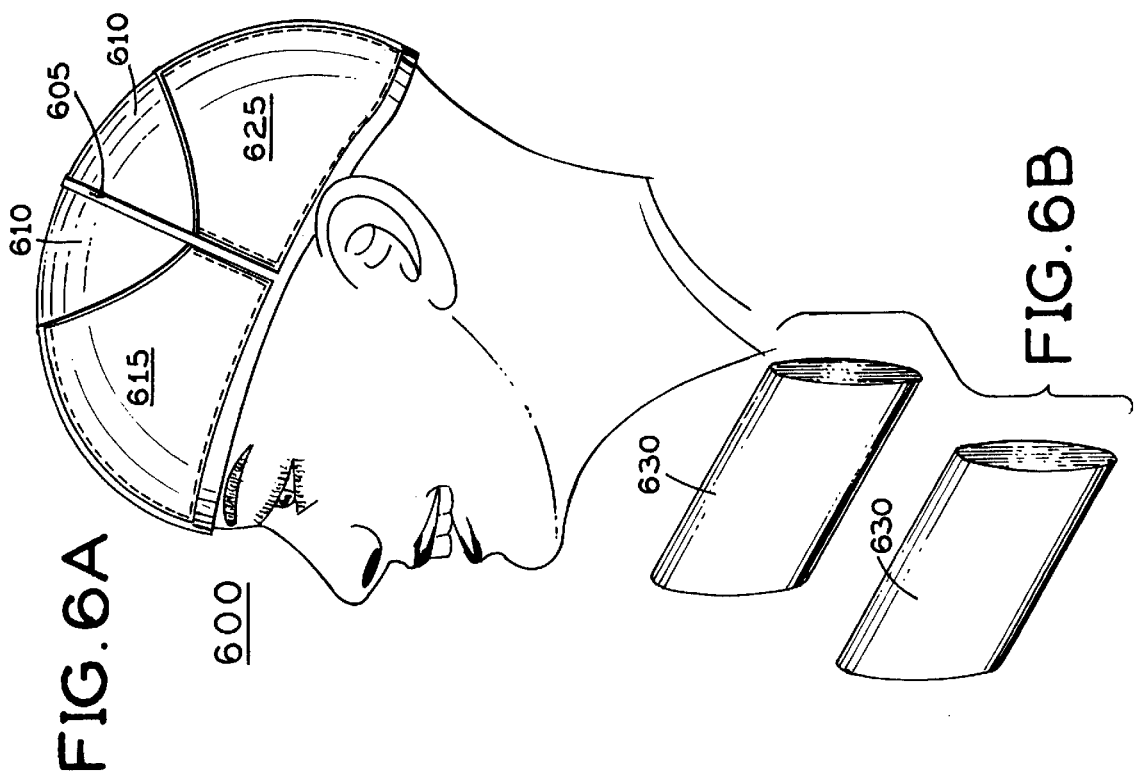
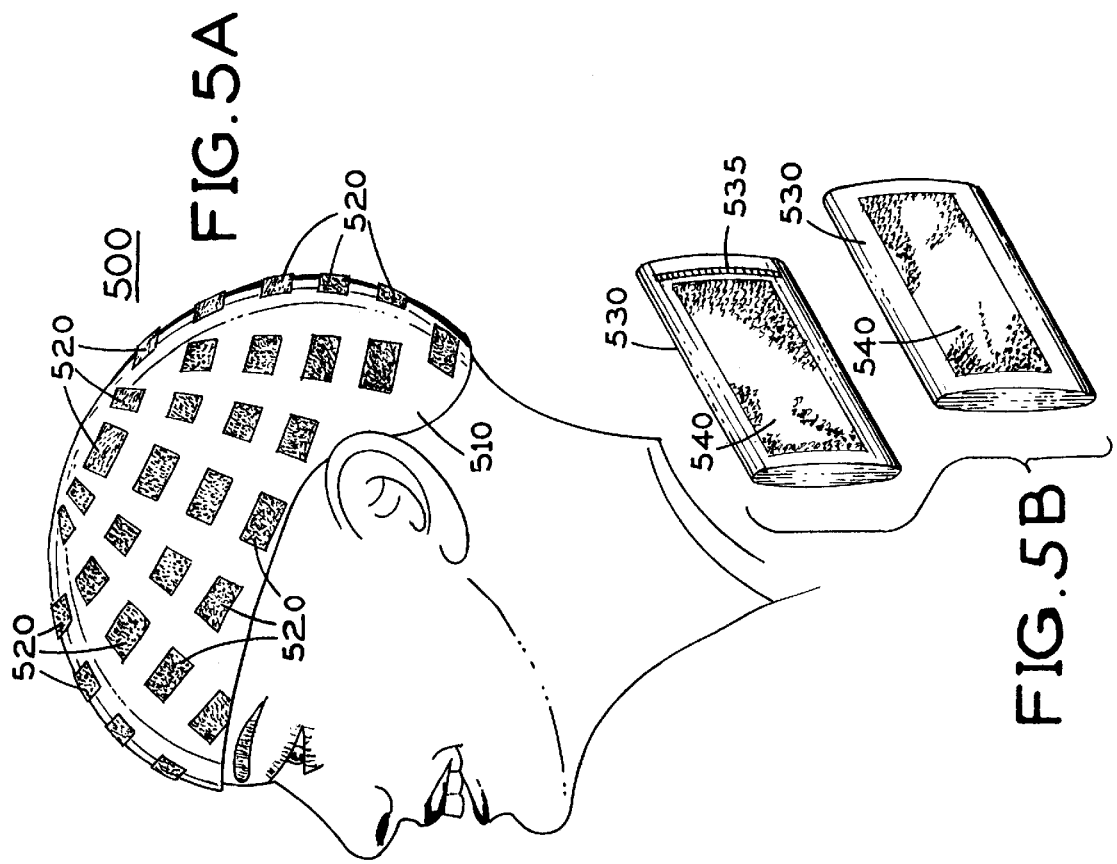

MULTICHAMBERED ICE CAP

This invention relates to icecaps, and in particular to a soft flexible cap (rubber, vinyl and the like) having a helmet shape to fit around a head having multichambered compartments for holding ice or coolant materials such as Kwik Kold®, Blue Ice®, Crylor Gel® and the like, to be used for relief from headaches, fevers and other pertinent medical conditions. The multichambers can provide selective relief as well as applications for the entire head.

BACKGROUND AND PRIOR ART

Icepacks having flexible bags have traditionally been used to hold ice and/or frozen water. These bags are generally used for helping with headaches and other medicinal purposes. However, as a headache remedy, the icepack bag is difficult to position and often does not stay in place on ones head. Bags by themselves are inherently not designed to fit the head of the user. As a headache remedy, the bag must be continuously balanced on the patient's head not allowing the patient to lie down. This constant balancing further inhibits the user from applying the bag and ice contents to selected and needed locations on ones head.

Several U.S. patents have been attempted to solve the above identified problems but with little success. U.S. Pat. No. 2,049,723 to Pomeranz describes a "rubber ice skull." However, this patent requires a single filling port for accessing the internal cavities. Thus, Pomeranz requires filling their entire device. Other patents describe elaborate and apparently uncomfortable strap and band contraptions to attach about one's head. See for example: U.S. Pat. Nos. 3,159,160 to Ullom; 3,491,761 to Baker; 3,696,814 to Umemoto; 4,138,743 to Elkins et al.; 4,356,709 to Alexander; 4,551,858 to Pasternack; 4,781,193 to Pagden; and 5,163,425 to Nambu et al.

Thus, the need exists for a solution to the above identified problems.

SUMMARY OF THE INVENTION

The first objective of the present invention is to provide a cold pack as an ice cap for the head that allows applications and coverage of all of the head regions and allows the patient to sit, lie in any position and to ambulate. The ice cap being comfortably held in place allowing complete or localized cold applications in a precise and steady manner.

The second object of this invention is to provide an ice cap having multichambered compartments allowing the patient to direct and position ice to a desired headtop location.

The third object of this invention is to provide a multichambered ice cap that can stretch to fit over different size heads of patients.

The fourth object of this invention is to provide an icecap that allows for localized applications of ice on ones head.

The novel invention aids for headache and fever relief. The invention can be used by paramedics and hospitals in head traumas to reduce swelling and bleeding: hypertensive encephalopath, and other medical conditions and indications such as but not limited to inflammatory pathology such as meningitis, encephalitis, sinusitis, TMJ, hypertensive headaches, neoplasms, vasculitis and the like.

Further objects and advantages of this invention will be apparent from the following detailed description of a presently preferred embodiment which is illustrated schematically in the accompanying drawings.

BRIEF DESCRIPTION OF THE FIGURES

FIG. 1A is a side view of a first preferred embodiment icecap.

FIG. 1B is a top view of the first preferred embodiment of FIG. 1A along arrow A.

FIG. 1C is a front partial view of the first preferred embodiment of FIG. 1B along arrow D with an optional septum wall.

FIG. 2A is a side view of a screw-on waterproof cap for use with the embodiment of FIGS. 1A–1B.

FIG. 2B is a side view of a push-in waterproof cap for use with the embodiment of FIGS. 1A–1B.

FIG. 3 is a side view of a second preferred embodiment icecap.

FIG. 4A is a side view of a third preferred embodiment icecap.

FIG. 5A is a side view of a fourth preferred embodiment icecap.

FIG. 5B is a perspective view of icecap pouches having hook and loop fasteners on one side.

FIG. 6A is a side view of a fifth preferred embodiment icecap.

FIG. 6B is a perspective view of icecap pouches for use with the fifth preferred embodiment.

DESCRIPTION OF THE PREFERRED EMBODIMENT

Figure 4C:
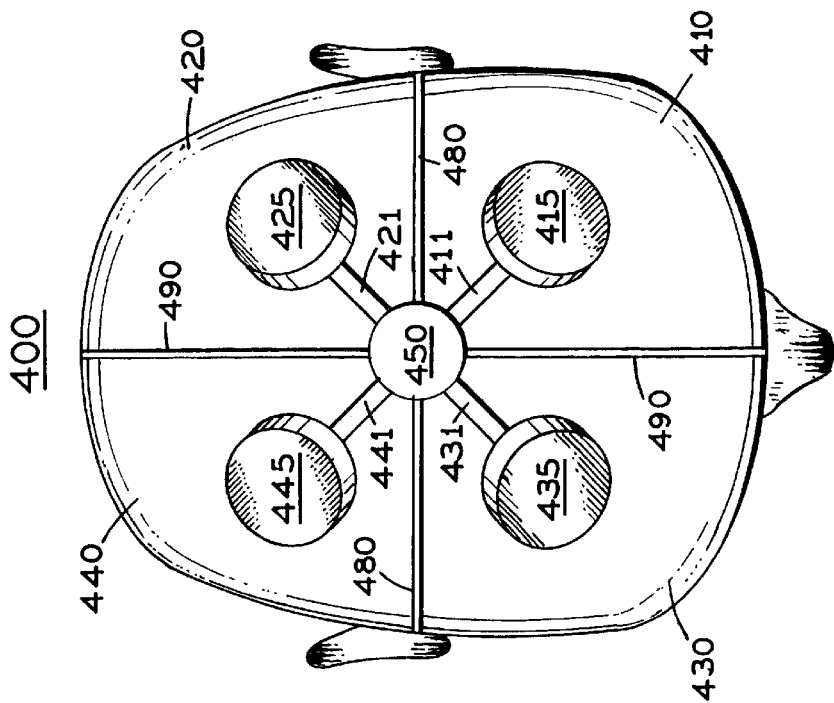
FIG. 4C is a top view of the third preferred embodiment icecap of FIG. 4B along arrow C.

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

FIG. 1A is a side view of a first preferred embodiment icecap 100. FIG. 1B is a top view of the first preferred embodiment 100 of FIG. 1A along arrow A. Referring to FIGS. 1A–1B, embodiment 100 includes a front top chamber 110, a left top chamber 120, a right top chamber 130, and an rear top chamber 140. Each chamber is designed to parallel the skull bones and has respective portals 115, 125, 135, and 145 which will be discussed in more detail in reference to FIGS. 2A–2B. Each chamber has a lower-inner flexible layer 112, 122, 132, 142 that conforms and closely abuts against the top of the head 3 of the user. Each chamber further has an upper flexible layer 114, 124, 134 and 144. Elastic bands 182, 184 and 186 sealingly separate the chambers from one another and allow for the icecap 100 to stretch and tightly be held on the head 3. Alternatively, flexible layers can be sized to stretch down to cover eyes and ears if needed. The Elastic bands can be formed from rubber, nylon, combinations thereof and the like. The inner and outer layers can be fastened to the elastic band walls by stitching, heat molding and the like. Similar elastic bands 172, 174 and 176 attach the sides of the cap embodiment 100 about the front 5 and sides 1, and ears 7, 9 of the user's head.

FIG. 1C is a front partial view of the first preferred embodiment of FIG. 1B along arrow D with an optional septum wall 116 which separates two frontal chambers 110A and 110B with a common portal 115B. Still further another version can have separate portals for both chambers 110A and 110B.

FIG. 2A is a side view of a screw-on waterproof cap portal 125 for use with the embodiment 100 of FIGS. 1A–1B. Cap portal 125 includes a screwable top cap portion 129 having inner threads which can be mateably screwable onto the threads of a base portion 128. The cap materials can be formed from rubber, plastic and the like, and be sealingly fastened to outer flexible layer 124 by stitching, heat molding and the like. FIG. 2B is a side view of an alternative push-in waterproof cap 125' for use with the embodiment 100 of FIGS. 1A–1B, and includes a plug cap type portion 129' attached by a pliable connection 126' to a base 128' which receives the plug 129'. Similar to FIG. 2A, base 128' is sealingly fastened to outer flexible layer 124 by stitching, heat molding and the like. The cap portals 125, 125' of FIGS. 2A–2B, are used to access each of the chambers and allow ice blocks, ice chips, crushed ice, blue ice®, and the like to be inserted therein. In use a single chamber, or any plural chambers can be filled through their respective portal caps so that selected areas of the head can have ice applied.

FIG. 3 is a side view of a second preferred embodiment icecap 200. Embodiment 200 is similar to embodiment 100 and includes like chambers and portals 210, 215, 220, 225, 230, 235 (not shown), 240 and 245, respectively. In this embodiment 200, a single elastic band 270 stretches from the front portion connection 272 of the cap 200 to rear connection portion 274. The remaining materials and connections are like those of the embodiment 100 of FIGS. 1A–1B.

Figure 4B:
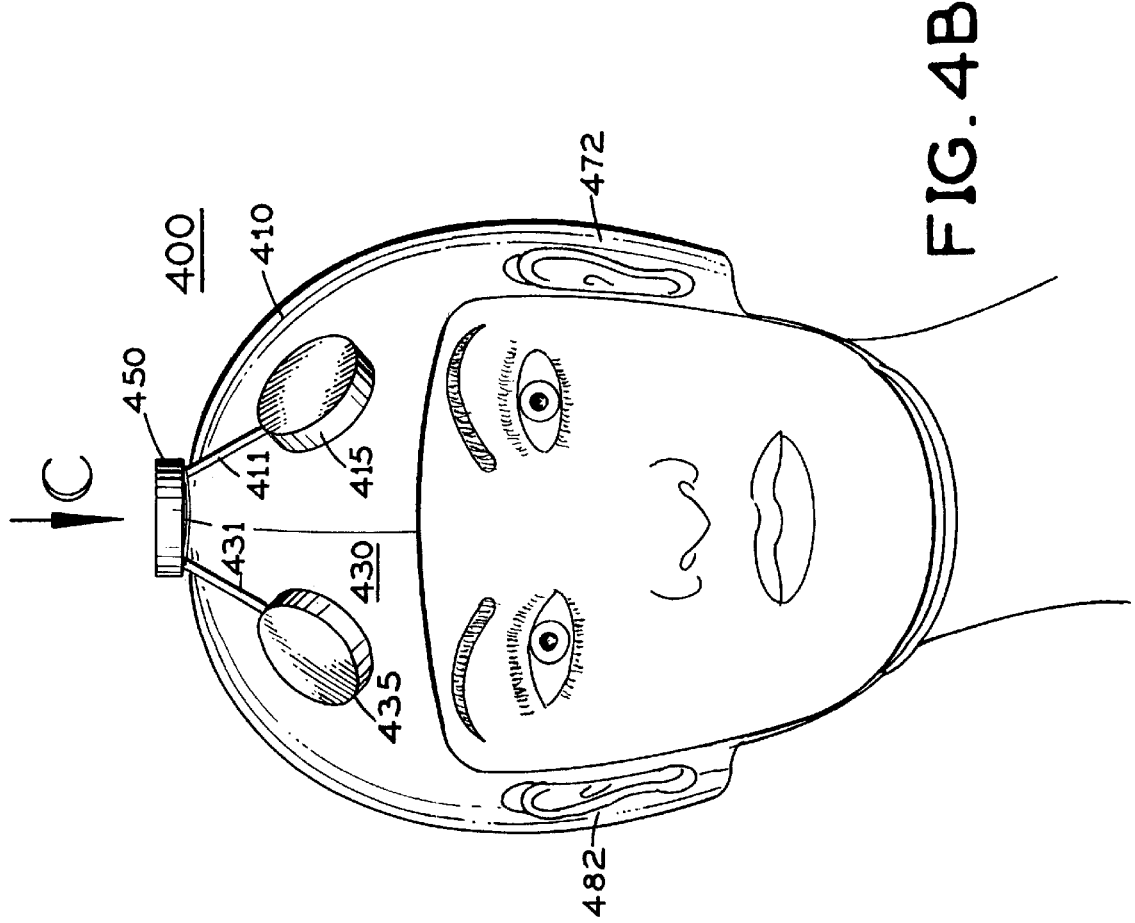
FIG. 4B is a front view of the third preferred embodiment icecap of FIG. 4A along arrow B.

FIG. 4A is a side view of a third preferred embodiment icecap 400. FIG. 4B is a front view of the third preferred embodiment icecap 400 of FIG. 4A along arrow B. FIG. 4C is a top view of the third preferred embodiment icecap 400 of FIG. 4B along arrow C. Embodiment 400 includes front top right chamber 410 with cap portal 415, front top left chamber 430 with cap portal 435, rear top right chamber 420 with cap portal 425, rear top left portal 440 with cap portal 445, each having materials and fastening connections similar to corresponding components of embodiment 100 of FIGS. 1A–1B. In embodiment 400 an elastic strap bands 411, 421, 431, 441 connect the cap portals 415, 425, 435, 445 to a top strap holder 450. Both the strap bands 411, 421, 431, 441 and holder 450 can be formed from plastic, nylon, rubber, combinations thereof and the like. Elastic bands 472, 474 and 476 can attach to the sides of the cap 400 by stitching, heat molding and the like. Similar to the previous embodiments, the chambers 410, 420, 430, 440, can be individually and selectively filled with ice and the like. Further elastic straps 480 and 490 can divide the cap 400 into separate compartments.

FIG. 5A is a side view of a fourth preferred embodiment icecap 500 having a single flexible surface layer in a helmet shape 510 along with hook and loop fasteners 520 such as Velcro® on the exterior surface. FIG. 5B is a perspective view of icecap pouches 530 having hook and loop fasteners 540 on one side. One or more pouches 530 each having cold fluid such as those previously described can be fastened at selected points on the exterior of the helmet shaped layer 510. Pouches 530 can be prefilled or alternatively have sealable zippered side openings 535, FIG. 6A is a side view of a fifth preferred embodiment icecap 600 having a single flexible surface layer 610 in a helmet shape. Flaps 615, 625 having sides attached by heat molding, sewing and the like, to the layer 610 form pockets. FIG. 6B is a perspective view of icecap pouches 630 similar to those of 530 discussed previously. Pouches 630 can be inserted into individual pockets 615 and 625 as needed. A septum wall 605 can separate the pockets from one another and can also be a detachable wall such as hook and loop fasteners, zippers and the like.

While the preferred embodiments show adult size human heads for using the icecaps, the invention can be sized in smaller sizes for pediatric use (children).

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A flexible ice cap to be worn on the head of a person comprising:

an inner semi-spherical layer and an outer semi-spherical flexible layer forming a cap body having a top portion and side portions including a left side and a right side;

said inner semi-spherical flexible layer having an upper surface and a lower side, the lower surface for fitting about top and side portions of a human head;

said outer semi-spherical flexible layer having an upper surface and a lower surface, the lower surface of the outer semi-spherical flexible layer overlying the upper surface of the inner semi-spherical flexible layer and forming at least two isolated levels of laterally separated and isolated chambers therebetweeen along the top and side portions of the human head, said levels being substantially horizontally separated relative to said top portion each of said levels being continuous from the left side to the right side of the cap body; and portals on the outer semi-spherical flexible layers, each portal opening to a chamber, wherein cold liquid can be poured discretely and exclusively into each selected chamber through a respective portal.

2. The flexible icecap of claim 1, wherein the inner semi-spherical flexible layer and the outer semi-spherical flexible layer are chosen from at least one of:

rubber, vinyl and hypoallergenic flexible materials.

3. The flexible icecap of claim 1, further comprising:

flexible straps for attaching each portal to a central attachment.

4. The flexible icecap of claim 1, further comprising:

a chin strap for holding the icecap in place.

5. The flexible icecap of claim 1, wherein the chambers and portals include:

a front top chamber and front top portal which parallels the frontal skull bones;

a left top chamber and a left top portal which parallels the left parietal skull bones;

a right top chamber and a right top portal which parallels the right parietal skull bones; and a rear top chamber and a rear top portal which parallels the occipital skull bones.

6. The flexible icecap of claim 5, further comprising:

a first elastic strap forming a wall between the front top chamber and both the left and the right top chambers;

a second elastic strap forming a separating wall between the right top chamber and the left top chamber; and a third elastic strap forming a separating wall between the rear top chamber and both the left and the right top chambers.

7. The flexible icecap of claim 1, wherein the chambers and portals include:

a front right top chamber and front right top portal;

a front left top chamber and a front left top portal;

a rear right top chamber and a rear right top portal; and a rear left top chamber and a rear left top portal.

8. The flexible icecap of claim 1, wherein each portal includes:

a screwable cap having interior threads; and a base portion having exterior threads mateable to the interior threads of the screwable cap.

9. The flexible icecap of claim 1, wherein each portal includes:

a plunger cap portion having a plug; and a base portion having an opening for receiving the plug of the cap portion.

10. The flexible icecap of claim 1, wherein the inner semispherical flexible layer and the outer semi-spherical flexible layer includes:

a helmet shape.

11. A flexible ice cap to be worn on the head of a person comprising:

an inner semi-spherical flexible layer having an upper side and a lower side, the lower side for fitting about top and side portions of a human head;

an outer semi-spherical flexible layer having an upper side and a lower side, the lower side of the outer semi-spherical flexible layer overlying the upper side of the inner semi-spherical flexible layer and forming separated and isolated chambers therebetween along the top portion of the human head; and portals on the upper side of the outer semi-spherical flexible layer, each portal opening to a chamber, wherein cold liquid can be poured selectively and discretely into each chamber through a respective portal;

detachable walls between each of the chambers, the detachable walls chosen from one of:

septums, zippers, and hook and loop fastener material; and wherein each chamber can be selectively filled with the cold liquid.

12. A flexible ice cap to be worn on the head of a person for medical applications, comprising:

a flexible single layer forming a cap body having a helmet shape with a top portion and side portions including a left side and a right side and an inner surface and an outer surface, the inner surface for abutting against the head of a user;

cap body hood and loop fasteners attached to the outer surface of the flexible layer; and at least two sealable pouches having pouch hook and loop fasteners and being sized for selective and simultaneous placement on said hook and loop fasteners along at least one level, said at least one level being substantially horizontal relative to said top portion of the cap, and further being continuous from the left side to the right side of the cap body; each pouch being attached and detachable along selected surfaces on the outer surface of the flexible single layer, wherein at least one selected said pouch can be prefilled with coolant liquid.

13. A flexible ice cap to be worn on the head of a person for medical applications, comprising:

a flexible single layer forming a cap body having a helmet shape with a top portion and side portions including a left side and a right side, and an inner surface and an outer surface, the inner surface for abutting against the head of a user;

a plurality of pockets arrayed along at least two levels which are substantially horizontal relative to said top portion of the cap, and which levels are continuous from the left side to the right side of the cap; each of said pockets having a side opening attached to the outer surface of the flexible layer, and at least two sealable pouches being individually sized for selective and simultaneous placement into said pockets along at least one of said substantially horizontal levels wherein the at least one said pouch can be prefilled with coolant liquid.

* * * * *